United States Patent [19]

Stevens et al.

[11] 3,966,596
[45] June 29, 1976

[54] HIGH PERFORMANCE, CATION-EXCHANGE CHROMATOGRAPHY ON SURFACE-SULFONATED COMPOSITIONS

[75] Inventors: Timothy S. Stevens; Hamish Small, both of Midland, Mich.

[73] Assignee: The Dow Chemical Company, Midland, Mich.

[22] Filed: Mar. 10, 1975

[21] Appl. No.: 556,761

Related U.S. Application Data

[63] Continuation-in-part of Ser. No. 386,261, Aug. 6, 1973, Pat. No. 3,925,019.

[52] U.S. Cl.................................. 210/24; 210/198 C
[51] Int. Cl.²......................................... B01D 15/08
[58] Field of Search............... 55/67, 386; 210/24 C, 210/198 C

[56] References Cited

UNITED STATES PATENTS

| | | | |
|---|---|---|---|
| 3,102,782 | 9/1963 | Small | 423/7 |
| 3,458,976 | 8/1969 | Hollis | 55/386 |
| 3,565,833 | 2/1971 | Battaerd | 260/2.1 |
| 3,725,260 | 4/1973 | Stalling et al. | 210/24 C |
| 3,827,989 | 8/1974 | Scott | 260/2.1 E |

FOREIGN PATENTS OR APPLICATIONS

| | | |
|---|---|---|
| 871,541 | 6/1961 | United Kingdom |
| 1,344,706 | 1/1974 | United Kingdom |

OTHER PUBLICATIONS

Analytical Chemistry, 39: 1422–1428, Horvath et al., 1967.
J. Chromatographic Science, 7: 109–116, Horvath et al., 1969.
Nature 207: 402–403, Parrish, 1965.
J. Chromatographic Science, 12: 458–463, 464–472, 1974.

*Primary Examiner*—John Adee
*Attorney, Agent, or Firm*—David H. Fifield

[57] ABSTRACT

A process for high performance, cation-exchange chromatography employing a cation-exchange composition comprising synthetic resin particles of about 5 to about 200 microns particle size, said synthetic resin particles being cross-linked to from about 0.25 to about 5% and surface-sulfonated to a calculated depth of about 100 to about 300 Angstroms is disclosed.

10 Claims, 5 Drawing Figures

HIGH PERFORMANCE, CATION-EXCHANGE CHROMATOGRAPHY ON SURFACE-SULFONATED COMPOSITIONS

CROSS-REFERENCE TO RELATED APPLICATION

This Application is a continuation-in-part of our copending Application, Ser. No. 386,261 filed Aug. 6, 1973, now U.S. Pat. No. 3,925,019.

BACKGROUND OF THE INVENTION

The invention pertains to a process for practicing high performance, cation-exchange chromatography. Materials for performing high speed, liquid chromatagraphic analyses are known where only the thin, outer surface of the chromatographic support material actively exchanges ions with a liquid medium.

Parrish, in Nature 207:402 (1965), describes "superficial ion-exchange chromatography" using beads of cross-linked polystyrene which bear a "shallow surface layer" of ion-exchange groups. The beads Parrish describes there are about 240 microns mean diameter and are surface-sulfonated, according to our calculations, to a depth of approximately 210 Angstroms. Small in U.S. Pat. No. 3,102,782 discloses surface-sulfonated styrene-divinyl benzene copolymer beads ranging from 0.5–8% cross-linking with capacities from which we calculate the depth of surface-sulfonation to be within the range contemplated for utilization in the present chromatographic process. The materials of Small were utilized for solvent extraction of heavy metal salts into a complexing organic solvent phase imbibed by the beads. There is no suggestion that compositions within the range of cross-linking and calculated depth of surface-sulfonation Small teaches would prove extremely useful in the practice of cation-exchange chromatography.

Others have described ion-exchange chromatography with materials having an impervious core, such as a glass bead or diatomaceous earth particle, coated with a skin-like layer of styrene-divinylbenzene resin which is appropriately sulfonated or aminated to produce, respectively, cation or anion-exchange materials, Analytical Chemistry 39:1422; British Pat. Nos. 871,541 and 1,344,706.

To our knowledge however, no previous artisan has noted the critical relation between the degree of cross-linking and the calculated depth of surface-sulfonation for such ion-exchange chromatographic support materials. Indeed, two articles by Hansen et al., J. Chrom. Sci. 12:458–463 and 464–472 (1974) speculate that in 8% cross-linked materials, the depth of the ion-exchanging surface layer should be about 2000 to about 7000 Angstroms to optimize performance in ion-exchange chromatography in resin particles of about 10 to 60 microns particle size. Horvath in J. Chrom. Sci. 7:109–116 (1969) concludes that the smaller the shell thickness in a "pellicular" packing for high pressure liquid chromatography, the smaller the contribution of the packing to reduced plate height of his chromatographic columns.

SUMMARY OF THE INVENTION

The invention is a process for chromatographic separation of cations which employs a composition of matter comprising synthetic resin particles of about 5 microns to about 200 microns particle size, said synthetic resin particles being cross-linked to from about 0.25 to about 5% and surface-sulfonated to a calculated depth of about 100 Angstroms to about 300 Angstroms.

In the composition, the synthetic resin particles preferably consist essentially of a poly(vinylaromatic) polymer and most preferably of a styrene-divinylbenzene copolymer of the above-stated degree of cross-linking. It is preferred that the synthetic resin particles be of about 20 microns to about 100 microns particle size and most preferably between about 35 and 75 microns particle size. The synthetic resin particles are preferably cross-linked to from about 1 percent to about 3.5 percent and most preferably from about 1.5 percent to about 2.5 percent. The synthetic resin particles are suitably surface-sulfonated to a calculated depth of about 100 Angstroms to about 300 Angstroms and are preferably surface-sulfonated to a calculated depth of about 150 Angstroms to about 250 Angstroms.

By "calculated depth of surface-sulfonation" we mean the depth of a layer, measured from the outer surface inward toward the interior of a synthetic resin particle, in which sulfonation of the resin is assumed to be essentially complete (e.g. about one sulfonate moiety per vinylaromatic moiety in poly(vinylaromatic) resin particles). Based on such a model, measured capacities of our compositions have been converted into calculated depths of surface-sulfonation from FIG. 1. This is discussed more fully in our Detailed Description of the Invention under the heading entitled "Calculated Depth of Surface-Sulfonation".

By "sulfonation" and "sulfonated" we refer to a well-known chemical process of introducing $-SO_3^-$ functional groups into the structure of synthetic resins and resins which have such groups attached to them. Any of the commonly known forms of the $-SO_3^-$ group is included in our defination unless otherwise stated. For example, both the acid form $-SO_3H$ and metallic salt form $-SO_3Na$, are within our definition.

By cross-linked we mean synthetic resins having, to some extent, polyfunctional moeities which serve to tie together linear resin backbones. Divinylbenzene is a common cross-linker for vinylaromatic resin systems. The degree of cross-linking to which we refer is the mole percent of cross-linker which is present in a pre-polymerization mixture of styrene and divinylbenzene. Other vinylaromatic resins with other cross-linkers may be related to styrene-divinylbenzene standards by well known solvent swelling tests. For polyethylene resins and other nonvinylaromatic materials, diffusion characteristics of the resins may be compared to standard styrene-divinylbenzene resins of known cross-linking by comparing half-neutralization times for fully sulfonated resins of each type, e.g. measuring the times required to neutralize half the capacity of resins. Comparable half-times will give comparable diffusion characteristics.

A process suitable for chromatographic separation of two or more cations comprises:

a. Passing a fluid mixture comprising the cations through a bed comprising synthetic resin particles of about 5 microns to about 200 microns particle size, said synthetic resin particles being cross-linked to from about 0.25 percent to about 5 percent and surface-sulfonated to a calculated depth of about 100 Angstroms to about 300 Angstroms; and b. Eluting the bed with an eluent which differentially removes cations which are attracted to surface-sulfonation sites on the synthetic particles.

The chromatographic process is preferably carried out upon a fluid mixture which comprises a liquid solution of the cations. Moreover, the process preferably employs a composition wherein the synthetic resin particles consist essentially of a poly(vinylaromatic) polymer and synthetic resin particles are preferably of about 20 microns to about 100 microns particle size.

This chromatographic separation process preferably employs a composition wherein the synthetic resin particles are cross-linked to from about 1 to about 3.5 percent. Most preferably, the chromatographic separation employs a composition wherein the synthetic resin particles consist essentially of styrene-divinylbenzene copolymer which is cross-linked to from about 1.5 percent to about 2.5 percent and whose synthetic resin particles are surface-sulfonated to a calculated depth of about 150 Angstroms to about 250 Angstroms.

DETAILED DESCRIPTION OF THE INVENTION

Composition Preparation

Figure 1:
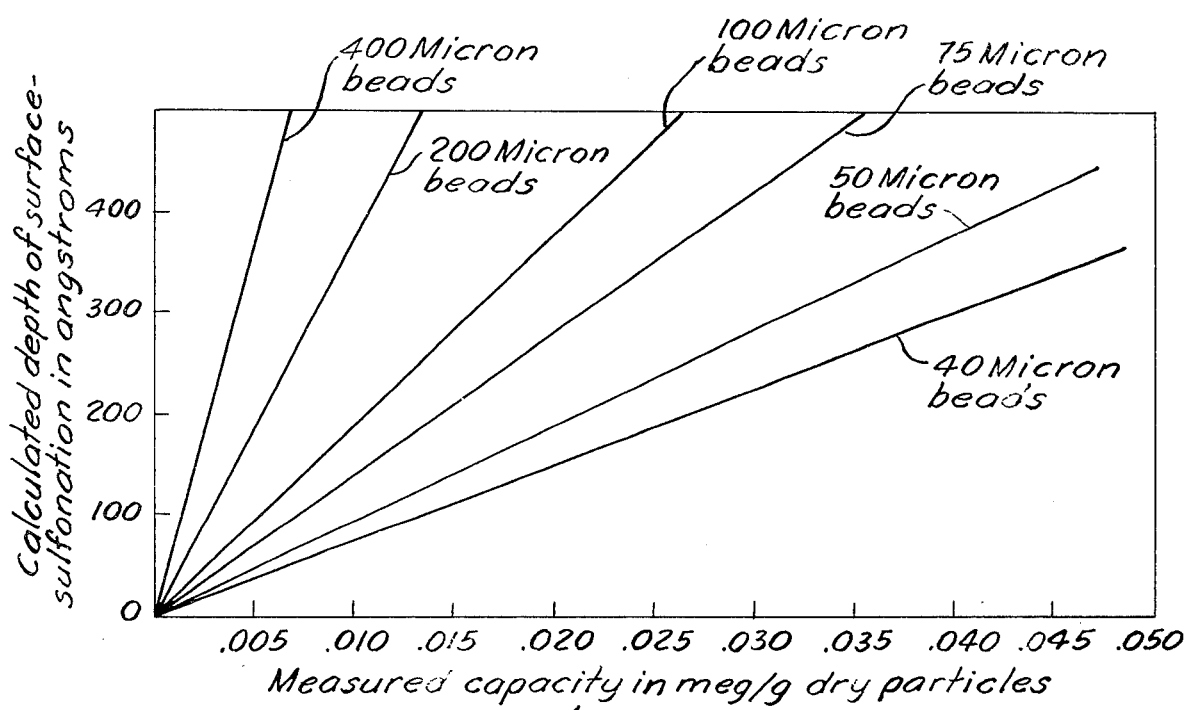
FIGS. 1 and 1a show the Calculated Depth of Surface-Sulfonation versus Measured Capacity, in graph form, for synthetic resin particles of various mean particle sizes.

The composition employed in the invention process comprises synthetic resin particles of about 5 microns to about 200 microns particle size or greater. The synthetic resin from which these particles are obtained may suitably be any synthetic resin material which is capable of being cross-linked to a degree which renders it insoluble in any solvent medium in which it will subsequently be employed and which is capable of being surface-sulfonated by means hereafter described. For example synthetic resins such as polyacrylic, polymethacrylic, poly(vinylaromatic), poly(phenol-formaldehyde), polyethylene resins and the like may be employed and may suitably be chosen from gel-type resins well known in the art. Preferred in the invention are poly(vinylaromatic) resins, with styrene-divinylbenzene copolymers most preferred.

Any commercially available resin of the type described above may be employed so long as it is cross-linked to a degree comparable to styrene-divinylbenzene within the specified range of about 0.25 to 5 percent. The composition's synthetic resin particles may be a mixture of any of the above-described resins which are capable of being surface-sulfonated as described.

The synthetic resin are commonly available commercially within certain particle size ranges and may be selected so as to fall within the designated particle size range of approximately 5 to 200 microns. If the synthetic resin is not available in the desired particle size range, particles larger than desired may be removed by screening synthetic resin particles through a standard sieve. Particles finer than desired may be removed by screening the synthetic resin particles with the appropriate size sieve. At the lower end of the particle size range (i.e. less than about 40 microns), separation may also suitably be obtained by centrifugation methods. It is also desirable, but not critical, to employ synthetic resin particles of a relatively narrow particle size distribution range. The particles which are preferred for the preparation of the composition used in the invention are particles which are substantially spherical in nature.

While below about 5 microns particle size surface-sulfonated synthetic resins are not significantly superior to completely sulfonated resins of the same size, due to practical problems of difficulty in achieving uniform packing in chromatographic columns and high pressures that must be handled by other more fragile components of the chromatographic apparatus, they may be beneficially employed if the apparatus and packing is suitable. Above about 200 microns particle size, the particle size is not critical and processes utilizing our preferred compositions of particle sizes this order of magnitude are beneficially employed. Faster elution speeds are attainable with larger size particles but columns must be lengthened proportionally to achieve resolution equivalent to that attained with shorter columns having smaller particle size packings. For this reasin, packings of about 5–200 microns particle sizes will be preferred as those skilled in the art generally prefer to use high-pressure columns of the shortest length possible.

Synthetic resins are commercially available which have sulfonic acid groups or metal sulfonate groups attached to their structure as cation-exchange functional sites. However, resins of the designated degree of cross-linking which are only sulfonated on their surface are not commercially available and must be specially prepared from the above-described synthetic resin particles of suitable cross-linking. This surface-sulfonation may be accomplished by contacting the synthetic resin particles with one of a number of chemical sulfonating agents, e.g. concentrated sulfuric acid, chlorosulfonic acid, liquid sulfur dioxide with or without sulfur trioxide or chlorosulfonic acid. We prefer to surface-sulfonate the synthetic resin particles using 96 percent sulfuric acid at a temperature of about 90° to about 100°C. by heating the sulfuric acid to that temperature and then contacting the synthetic resin particles with the heated acid solution for about 1 to about 10 minutes or more, depending on the depth of sulfonation desired.

Sulfonation occurs by penetration of the sulfonating agent into the resin particles from the outer surface inward. For this reason, the depth of sulfonation may be controlled by adjusting the temperature of the acid or the time of contact of the resin particles with the acid. The speed of penetration by the sulfonating agent increases with the temperature. Therefore, at a higher temperature, less contact time will be required to attain the same calculated depth of surface-sulfonation. When sulfonation has proceeded for the time desired, the sulfuric acid-synthetic resin particle mixture is poured with a circular motion into a large volume of distilled water. Extreme caution must be observed during this step of the operation since the contact of concentrated sulfuric acid with water may cause the acid to be splattered. Therefore, suitable protective clothing and shielding materials should be employed.

If the acid temperature and the time of contact are carefully controlled, the calculated depth of surface-sulfonation may be rather closely reproduced provided that the synthetic resin particles of about the same size distribution range and from the same batch of resin are employed. Surface-sulfonation of the calculated depth desired may be obtained by first carrying out the sulfonation procedure at about 95°C. with a contact time of about 2 minutes, computing the calculated depth of surface-sulfonation and then adjusting time or temperature upward or downward to attain a calculated depth of surface-sulfonation greater or less, respectively, than the first calculated depth obtained at 95°C. and 2 minutes.

While we have described our method for preparing the surface-sulfonated compositions to be employed in our chromatographic process, preferred due to the simplicity and inexpensive nature of the preparation, other means may be employed so long as the surface-sulfonated layer of the particles is of the degree of cross-linking stated and is sulfonated to the calculated depth set out above.

For example, fully sulfonated resin beads of the degree of cross-linking we have described may be treated in such a manner as to immobilize their cores and to render all but their surface layer, of prescribed thickness, impervious to cations by methods described in USP 3,827,989. There, beads are imbided with cross-linker such as DVB which is then polymerized in situ in the core while retaining an outer layer of unimbibed resin by briefly extracting the imbibed cross-linker with methanol from the surface of the beads. Briefer contact with methanol would result in a thinner unimbibed outer layer as we desire. Alternatively, a thin layer of soluble resin containing the required quantity of cross-linker may be coated to the prescribed 100–300 Angstroms thickness on an inert core such as a glass bead then polymerized in situ. The layer is then fully sulfonated, as in Br. Pat. No. 1,344,706, except that the film of resin should be much thinner than employed therein.

CALCULATED DEPTH OF SURFACE-SULFONATION

Figure 1A:
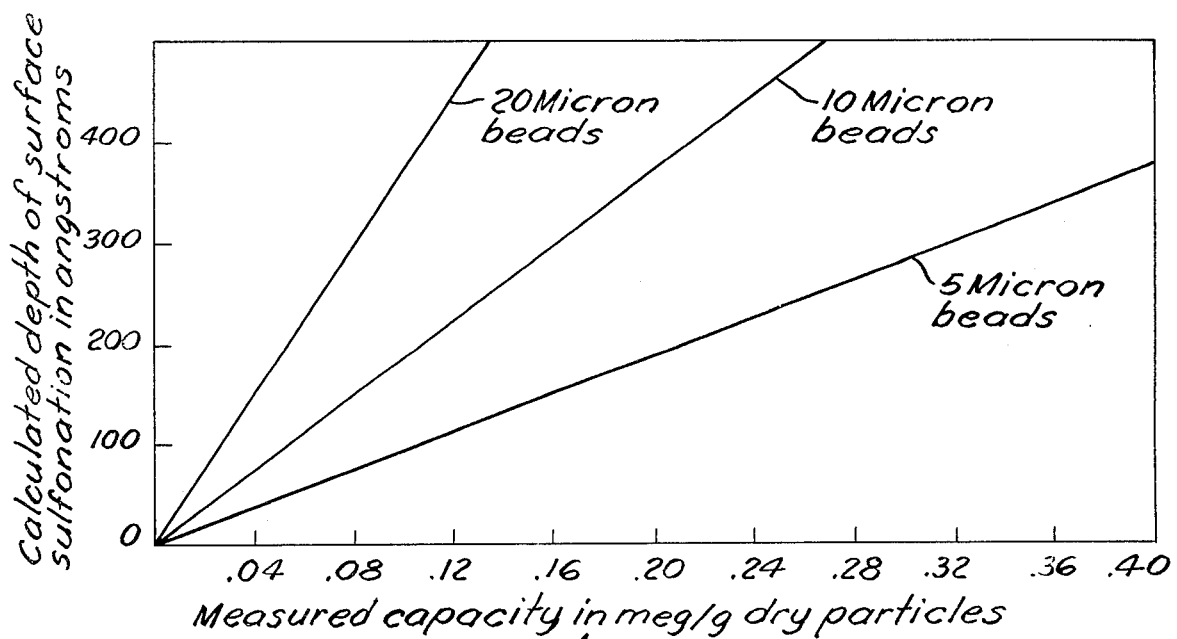

While the actual depth of surface-sulfonation may be determined by employment of a relatively new technique known as Auger spectroscopy, we determine the calculated depth of surface-sulfonation from data obtained by relatively simple experimental methods. This is accomplished by titrating a known dry weight of the synthetic resin particles with a standard strong base such as sodium hydroxide to determine the capacity in milliequivalents per gram (meq/g) of the dry synthetic resin particles. Assuming that the particle size distribution falls along the common Gaussian bell-shaped curve and knowing the mean particle size, one can calculate the approximate surface area of a gram of the dry synthetic particles assuming that the particles are substantially spheroidal in shape. From these calculations, we have established the relationship between the calculated depth of surface-sulfonation and the capacity of the resins in meq/g of dry resin particles for resin particles of various mean particle sizes, assuming that sulfonation is essentially complete in a sharply defined surface layer as mentioned earlier. This relationship is shown in FIGS. 1 and 1a and from these Figures, the calculated depth of surface-sulfonation for synthetic resin particles of a known mean particle size and a known capacity may be determined.

CATION-EXCHANGE CHROMATOGRAPHIC SEPARATION

The chromatographic separation contemplated here is suitably carried out in a stationary bed so that the fluid mixture may be passed through the bed with a suitable eluent to chromatographically separate the different cations in the fluid mixture which are attracted to the surface-sulfonation sites on the synthetic resin particles. Preferably, the fluid mixture comprises a liquid solution of the cations to be chromatographically separated. The process is preferably carried out by passing a fluid mixture comprising a liquid solution of cations through a bed comprising the synthetic resin particles and the sulfonate groups on the synthetic resin particles are, prior to contact with the mixture, predominately in the acid form. In another preferred embodiment, the process is utilized for the chromatographic separation of a liquid solution of cations which comprises sodium and potassium cations.

In order to effect a chromatographic separation, an eluent which also possesses attraction for the cation-exchanging sites on the surface of the synthetic resin particles is passed through the fixed bed, ordinarily a column packed with the composition. This may be done either simultaneously with or after the mixture of cations is fed to the column in order to "push" the cations through the column so that they may be collected or analyzed as they come off the other end of the column. Such eluents will conveniently be liquid solutions of an ionic material which will regenerate the cation-exchanging sites on the surface of the synthetic resin particles, suitably to the form which they had prior to contact with the mixture of cations. The eluent will differentially remove cations which are attracted to surface-sulfonation sites on the synthetic resin particles.

The eluent is normally chosen so that its cationic species is different from the cations to be resolved so that there is no error introduced in any subsequent analysis of the resolved cations. Eluents to be employed in chromatographic separations are well known in the art and include materials such as strong inorganic acids or solutions of strongly dissociated organic compounds having an available hydrogen proton. One skilled in the art will be able to select suitable eluent systems depending on the type of cations to be resolved.

SPECIFIC EMBODIMENTS OF THE INVENTION

In the following examples, the synthetic resins' particle sizes have been determined by screening the styrene-divinylbenzene resin particles through a conventional sieve series to give particles of a size falling within the stated distribution range. The styrene-divinylbenzene (herein after S-DBV) resin particles were substantially spherical beads prepared from prepolymer mixes of known DVB monomer weight content. The S-DVB beads were surface-sulfonated by dumping the sieved copolymer beads into about 100 milliliters of 96 percent of sulfuric acid which had been heated to about 90°–100°C and mixed with the hot sulfuric acid for a specific time-measured by a stop watch. At the end of this time the reaction was quenched by pouring the slurry, with a circular motion, into about 2 liters of distilled water. The resin beads were then filtered out on a course glass sinter and washed with distilled water several times. The washed resin was placed in a beaker and tirated with standardized 0.1 molar sodium hydroxide solution to a pH of 7. The resin capacity was then determined from the weight of starting copolymer and the milliequivalents of sodium hydroxide required for titration.

A number of chromatographic separations were carried out employing standard 0.1 ml samples which each contained 1.1 microgram of sodium ion and 3.4 micrograms of potassium ion. The samples were eluted with 0.01 molar hydrochloric acid at a flow rate of from about 6 to about 62 cm/min linear velocity. The surface-sulfonated resin beads were packed into chromatographic columns of 2.8 mm internal diameter and 300 mm length; also into columns of 9 mm internal diameter by 125 mm length. In each run, a stripper column was connected in series, after the analytical column (containing the surface-sulfonated composition). The stripper column was packed with an ion exchange resin in the OH⁻ form and served to neutralize the acidic eluent and to remove chloride ions from the samples eluted from the analytical column and to convert the resolved cations to their OH⁻ coion form. The resolution between potassium and sodium cations was then measured with a conductivity meter which monitored the effluent from the stripper column. Hence, the stripper column served to eliminate interfering acid eluent. In the case of the 2.8 mm internal diameter analytical column, a 2.8 × 300 mm stripper column was used and in the case of the 9 mm internal diameter analytical column, a 9 × 250 mm stripper column was employed. The packing for the stripper column was a strong base ion-exchange resin sold under the name of DOWEX 1×8 Anion Exchange Resin which was about 8 percent cross-linked.

Since the physical parameter measured was the conductivity of the stripper column effluent, conductivity versus the amount of effluent flow (in ml) past the conductivity cell was electronically graphed to give the chromatographic data reported herein. Data was collected in terms of triangulated peak width at baseline in ml, separation between sodium and potassium peak maxima in ml and the linear velocity of the eluent (elution speed in cm/min).

Because one packing may result in complete resolution of the two components in 10 minutes, while another packing may result in only partial resolution but in 3 minutes, it is difficult to evaluate the performance of such packings and to determine which is the better packing. For this reason, the resins employed as chromatographic packings were evaluated on the basis of the resolution attained between the 1.1 microgram sample of sodium ion and the 3.4 microgram sample of potassium ion by calculating for a peak to peak maxima separation of 4 ml of eluent flow. The data needed was obtained from chromatograms by triangulating peaks to the base line and measuring, in ml, the peak to peak separation and the triangle base width of each peak. Resolution is calculated according to this equation:

$$R_o = \frac{V_2 - V_1}{(W_2 + W_1)/2} \qquad \text{Equation I}$$

where $V_2 - V_1$ is the peak to peak maxima separation and $W_1$ and $W_2$ are the triangulated peak widths.

If the length of the chromatographic column is doubled, the separation of the two peaks ($V_2 - V_1 = S$) will be doubled but the resulting resolution will not be. If a column is doubled, the resolution is improved by only the square root of 2, i.e. the resolution is proportional to the square root of separation. To compare the various surface-sulfonated compositions used in our process among themselves and with commercially available cation exchange chromatographic packings, the resolution data was transformed to give a calculated resolution between sodium and potassium ions as if the separation (S) between sodium ion and potassium ion were 4 ml. This transformation is shown in the equation below where $R_{tr}$ is the transformed resolution:

$$R_{tr} = \frac{\sqrt{S}\, R_o}{\sqrt{S_o}} = \frac{\sqrt{4\text{ml}}\, R_o}{\sqrt{S_o}} \qquad \text{Equation II}$$

$R_o$ is the resolution originally calculated from Equation I and $S_o$ is the separation ($V_2 - V_1$) originally seen on the chromatogram. In this manner, the resolution and separation data determined experimentally can be transformed in a manner that allows comparison of resolutions of different packings for a constant separation. Under these conditions, the higher the value of $R_{tr}$, the better the performance of the packing that was employed in the analytical column. This comparison is valid for different packings of not too dissimilar chromatographic characteristics.

Example 1-Performance as a Function of Cross-linking

Figure 2:
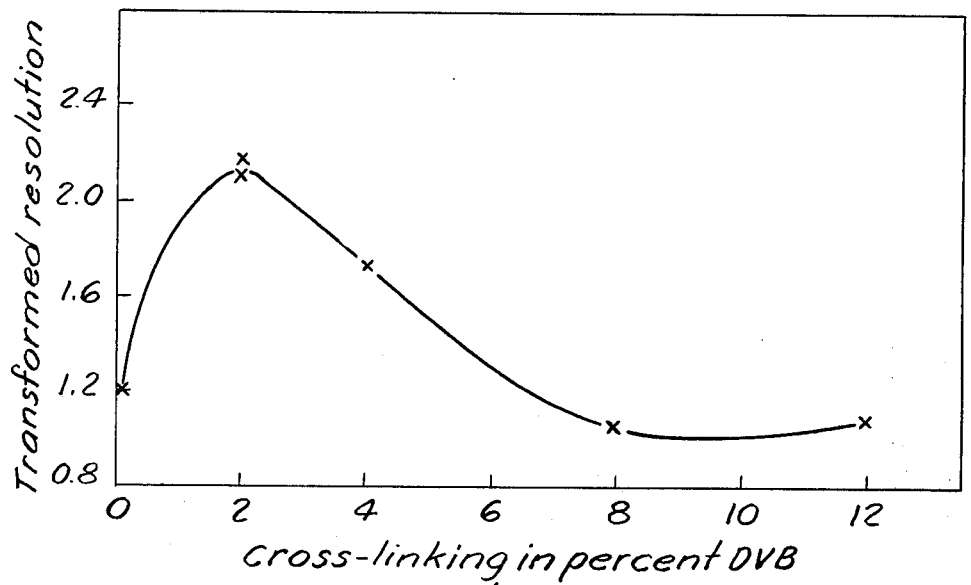
FIG. 2 shows the graph of Transformed Resolution versus Cross-Linking, from Table I.

In the manner described above, samples of the standard solution of sodium and potassium ions were eluted on 2.8 × 300 mm analytical columns with 9 × 250 mm stripper columns. The packing of the analytical columns were styrene-divinylbenzene copolymers ranging from 0.04 up to about 12 percent cross-linking which range from about 0.020 to about 0.030 meq/g surface-sulfonation capacity. This was approximately 190 Angstroms to about 280 Angstroms calculated surface-sulfonation depth as determined from FIG. 1. The beads were screened through 230 on 325 U.S. mesh sieve to give a mean bead size of approximately 50 microns. The precise parameters of the six compositions with different degrees of cross-linking are shown below in Table I with the experimental data obtained from elution of the potassium-sodium standard at various elution speeds. $S_o$ is the observed separation between the sodium and potassium ions peak maxima and $R_o$ is the resolution calculated from Equation I. $R_{tr}$ is the transformed resolution calculated from Equation II for a hypothetical peak maxima separation, S, of 4 ml. The transformed resolution for Runs 1–6(a) with common elution speed of 15.6 cm/min is graphed in FIG. 2, from the data shown in Table I, as a function of increasing cross-linking. As may be noted in FIG. 2, a distinct improvement is obtained in the transformed resolution, i.e. the performance of the composition, between about a quarter percent and about 5 percent cross-linking when a calculated surface-sulfonation depth is maintained within the range prescribed for the composition.

TABLE I

| Run No. | Elution Speed (cm/min) | $S_o$ (ml) | $R_o$ | if S were | $R_{tr}$ would be |
|---|---|---|---|---|---|
| 1a | 15.6 | 1.44 | 0.72 | 4 ml | 1.20 |
| 2a | 15.6 | 2.59 | 1.69 | " | 2.10 |
| 2b | 31.2 | 2.67 | 1.59 | " | 1.95 |
| 2c | 62.3 | 2.68 | 1.40 | " | 1.71 |

TABLE I-continued

| Run No. | Elution Speed (cm/min) | $S_o$ (ml) | $R_o$ | if S were | $R_{tr}$ would be |
|---|---|---|---|---|---|
| 3a | 15.6 | 2.40 | 1.67 | " | 2.16 |
| 3b | 31.2 | 2.50 | 1.68 | " | 2.13 |
| 3c | 62.3 | 2.53 | 1.57 | " | 1.97 |
| 4a | 15.6 | 3.36 | 1.59 | " | 1.73 |
| 4b | 31.2 | 3.30 | 1.51 | " | 1.66 |
| 4c | 62.3 | 3.37 | 1.43 | " | 1.56 |
| 5a | 15.6 | 2.74 | 0.88 | " | 1.06 |
| 5b | 31.2 | 2.80 | 0.80 | " | 0.96 |
| 5c | 62.3 | 2.76 | 0.72 | " | 0.87 |
| 6a | 15.6 | 2.11 | 0.79 | " | 1.09 |
| 6b | 31.2 | 1.97 | 0.79 | " | 1.13 |
| 6c | 62.3 | 1.95 | 0.78 | " | 1.12 |

Run 1 — 0.04% X-link; ~50μ bead size (230–325 U.S. mesh); ~280 A sulfonation depth** (0.030 meq/g)
Run 2 — 2% X-link; " " ; ~205 A sulfonation depth** (0.022 meq/g)
Run 3 — 2% X-link; " " ; ~215 A sulfonation depth** (0.023 meq/g)
Run 4 — 4% X-link; " (230–270 U.S. mesh); ~235 A sulfonation depth** (0.025 meq/g)
Run 5 — 8% X-link; " (320–325 U.S. mesh); ~190 A sulfonation depth** (0.020 meq/g)
Run 6 — 12% X-link; " " ; ~205 A sulfonation depth** (0.022 meq/g)

*Calculated from Equation II
**Calculated from Figure 1

Figure 3:
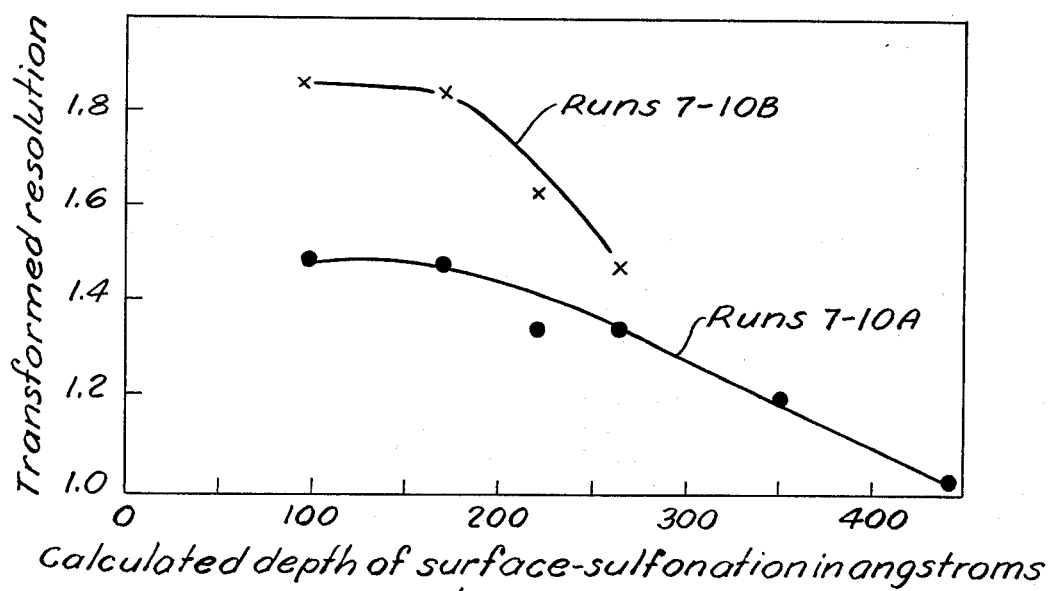
FIG. 3 shows the graph of Transformed Resolution versus Calculated Depth of Surface-Sulfonation, from Table II.

Example 2-Chromatographic Performance as a Function of Surface-Sulfonation Depth In this example, runs were made on resin beads of 2 percent cross-linked styrene-divinylbenzene resin which had been screened through 230 and on 325 U.S. mesh sieves, i.e. about 50 micron mean bead size, and which were surface-sulfonated at between about 90°–100°C for varying times to give different calculated depths of surface-sulfonation. Once again, a standard sodium-potassium ion sample was eluted on 9 × 125 mm analytical columns packed with the compositions of varying calculated depths of surface-sulfonation; 9 × 250 mm stripper columns were employed. Runs on all compositions were made at elution speeds of 12.1 cm/min and the majority of the compositions were also tested at elution speeds of 6.0 cm/min. The exact nature of the composition used in each Run is described below and the data obtained from these comparative elutions is contained in Table II below. $R_{tr}$ is plotted as a function of increasing calculated depth of surface-sulfonation on FIG. 3 for both elution speeds.

Example 3-Comparative Chromatographic Separations With Commercial Chromatographic Strong Cation Exchange Resins These series of runs were carried out to determine the performance of the invention methods, using our composition, relative to performance of methods using commercially available cation-exchange chromatographic packings. Runs were carried out using 2.8 × 300 mm analytical columns with a 2.8 × 300 mm stripper column in each case. The composition employed in our method was a styrene-divinylbenzene resin of about 2 percent cross-linking and about 40 microns mean bead size, i.e. screened through 325 on 400 U.S. mesh sieve. The resin beads were surface-sulfonated to a capacity of about 0.023 meq/g, a calculated depth of about 170 Angstroms as determined from FIG. 1. The packings used for comparison were DuPont's ZIPAX SCX Chromatographic Packing with a mean bead size of about 40μ and a cation-exchange capacity of about 0.010 meq/g; Reeve Angel's HS PELLIONEX SCX Chromatographic Packing of a mean bead size of about 40μ and a capacity of about 0.01 meq/g; and a Reeve Angel HC PELLIONEX SCX Chromatographic Pack-

TABLE II

| Run No. | Elution Speed (cm/min) | $S_o$ (ml) | $R_o$ | if S were | * $R_{tr}$ would be |
|---|---|---|---|---|---|
| 7a | 12.1 | 4.88 | 1.63 | 4 ml | 1.48 |
| 7b | 6.0 | 4.49 | 1.97 | " | 1.86 |
| 8a | 12.1 | 11.8 | 2.55 | " | 1.48 |
| 8b | 6.0 | 11.2 | 3.08 | " | 1.84 |
| 9a | 12.1 | 15.4 | 2.63 | " | 1.34 |
| 9b | 6.0 | 14.9 | 3.15 | " | 1.63 |
| 10a | 12.1 | 21.5 | 3.10 | " | 1.34 |
| 10b | 6.0 | 21.0 | 3.39 | " | 1.48 |
| 11a | 12.1 | 32.9 | 3.45 | " | 1.20 |
| 12a | 12.1 | 42.8 | 3.36 | " | 1.03 |

Run 7 — Sulfonated 1 min at 90°C.; ~95 A sulfonation depth** (0.010 meq/g)
Run 8 — Sulfonated 2 min at 90°C.; ~170 A sulfonation depth** (0.018 meq/g)
Run 9 — Sulfonated 1 min at 100°C.; ~220 A sulfonation depth** (0.023 meq/g)
Run 10 — Sulfonated 4 min at 90°C.; ~265 A sulfonation depth** (0.028 meq/g)
Run 11 — Sulfonated 1.5 min at 100°C.; ~350 A sulfonation depth** (0.037 meq/g)
Run 12 — Sulfonated 8 min at 90°C.; ~440 A sulfonation depth** (0.047 meq/g)

Figure 4:
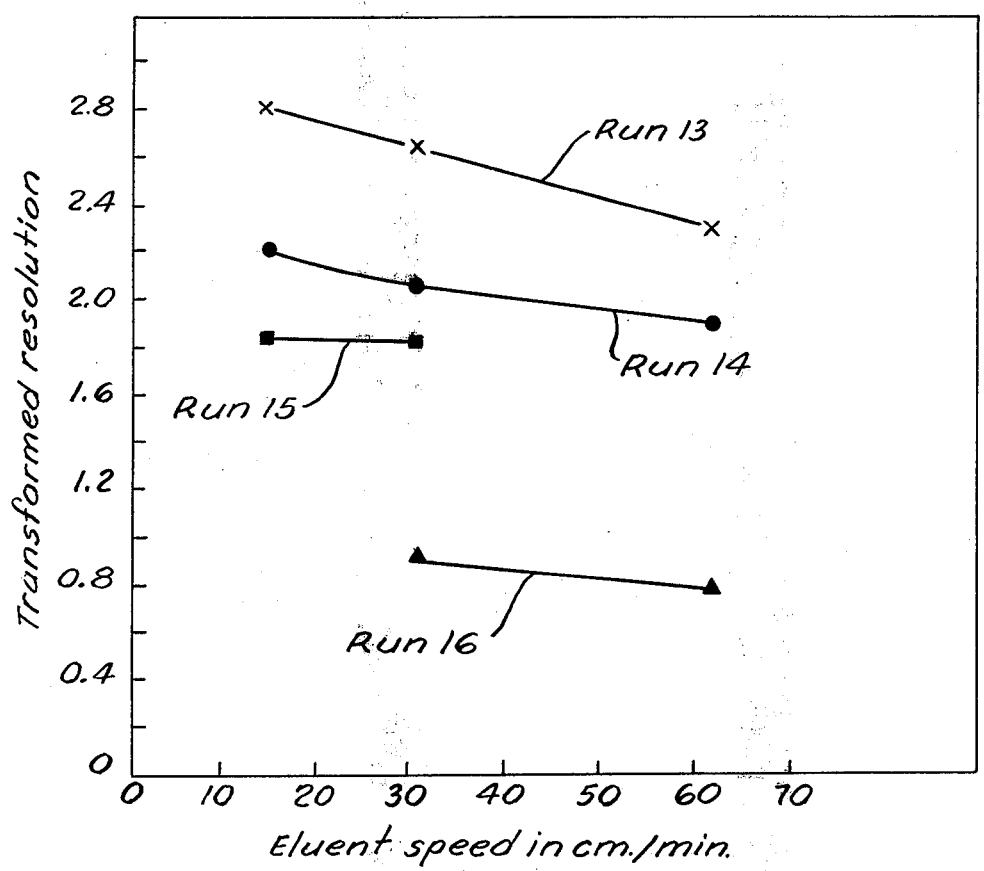
FIG. 4 shows the graph of Transformed Resolution versus Elution Speed for various packings, from Table III.

*Calculated from Equation II
**Calculated from Figure 1 ing of about 40μ mean bead size and of capacity of about 0.06 meq/g. Once again, standard sodium-potassium ion samples were eluted with elution speeds varying from about 15 to about 62 cm/min. Runs 13a-c employed our above-described, surface-sulfonated composition. Runs 14a-c employed the ZIPAX SCX Chromatographic Packing. Runs 15a-b employed the HS PELLIONEX SCX Chromatographic Packing. Runs 16b-c employed the HC PELLIONEX SCX Chromatographic Packing. Transformed resolution, $R_{tr}$, is plotted as a function of elution speed in the graph of FIG. 4, for each packing.

TABLE III

| Run No. | Elution Speed (cm/min) | $S_o$ (ml) | $R_o$ | if S were | $R_{tr}$ would be* |
|---|---|---|---|---|---|
| 13a | 15.6 | 1.63 | 1.79 | 4 ml | 2.80 |
| 13b | 31.2 | 1.63 | 1.67 | " | 2.62 |
| 13c | 62.3 | 1.57 | 1.44 | " | 2.30 |
| 14a | 15.6 | 3.26 | 2.00 | " | 2.22 |
| 14b | 31.2 | 3.26 | 1.86 | " | 2.06 |
| 14c | 62.3 | 3.33 | 1.74 | " | 1.91 |
| 15a | 15.6 | 0.57 | 0.69 | " | 1.83 |
| 15b | 31.2 | 0.55 | 0.67 | " | 1.81 |
| 16b | 31.2 | 31.1 | 2.48 | " | 0.89 |
| 16c | 62.3 | 30.3 | 2.15 | " | 0.78 |

*Calculated from Equation II

We claim:
1. A process for chromatographic separation of cations comprising:
   a. passing a fluid mixture comprising the cations through a bed comprising synthetic resin particles of about 5 microns to about 200 microns particle size, said synthetic resin particles being cross-linked to from about 0.25 percent to about 5 percent and surface-sulfonated to a calculated depth of about 100 Angstroms to about 300 Angstroms; and
   b. eluting the bed with an eluent which differentially removes cations which are attracted to surface-sulfonation sites on the synthetic resin particles.

2. A process described in claim 1 wherein the synthetic resin particles consist essentially of a poly(vinylaromatic) polymer.

3. A process described in claim 1 wherein the synthetic resin particles are of about 20 microns to about 100 microns particle size.

4. A process described in claim 1 wherein the synthetic resin particles are cross-linked to from about 1 percent to about 3.5 percent.

5. A process described in claim 1 wherein the synthetic resin particles are surface-sulfonated to a calculated depth of about 150 Angstroms to about 250 Angstroms.

6. A process described in claim 1 wherein the synthetic resin particles consist essentially of styrene-divinylbenzene copolymer which is cross-linked to from about 1 percent to about 3.5 percent and wherein said synthetic resin particles are of about 20 microns to about 100 microns particle size.

7. A process described in claim 6 wherein the synthetic resin particles are surface-sulfonated to a calculated depth of about 150 Angstroms to about 250 Angstroms and the sytrene-divinylbenzene copolymer is cross-linked to from about 1.5 percent to about 2.5 percent.

8. A process described in claim 1 wherein the fluid mixture comprises a liquid solution of the cations and sulfonate groups, prior to step (a), are predominately in the acid form.

9. A process described in claim 8 wherein the liquid solution comprises sodium and potassium cations.

10. A process described in claim 8 wherein the synthetic resin particles consist essentially of styrene-divinylbenzene copolymer which is cross-linked to from about 1.5 percent to about 2.5 percent and said synthetic resin particles are surface-sulfonated to a calculated depth of about 150 Angstroms to about 250 Angstroms and the eluent comprises an aqueous hydrochloric acid solution.

* * * * *

UNITED STATES PATENT AND TRADEMARK OFFICE
CERTIFICATE OF CORRECTION

PATENT NO. : 3,966,596
DATED : June 29, 1976
INVENTOR(S) : Timothy S. Stevens; Hamish Small It is certified that error appears in the above-identified patent and that said Letters Patent are hereby corrected as shown below:

Column 1, line 34, "range" should read --ranges--;

Column 2, line 40, "moeities" should read --moieties--;

Column 4, line 24, "reasin" should read --reason--;

Column 7, line 14, "OH$^-$" should read --OH$^\ominus$--;

Column 7, line 17, "OH$^-$" should read --OH$^\ominus$--;

Column 8, Table I, the last heading should read --R$_{tr}^*$ would be--;

Column 9, Table I, the last heading should read --R$_{tr}^*$ would be--;

Column 12, line 31, "sytrene-divinylbenzene" should read --styrene-divinylbenzene--.

Signed and Sealed this

Seventh Day of December 1976

[SEAL]

Attest:

RUTH C. MASON
Attesting Officer

C. MARSHALL DANN
Commissioner of Patents and Trademarks